(12) United States Patent
Haldeman et al.

(10) Patent No.: US 12,057,681 B1
(45) Date of Patent: Aug. 6, 2024

(54) SELF-POWERED IONIZATION DEVICE

(71) Applicants: Robert Blake Haldeman, Port Orange, FL (US); Robert Bruce Haldeman, Port Orange, FL (US)

(72) Inventors: Robert Blake Haldeman, Port Orange, FL (US); Robert Bruce Haldeman, Port Orange, FL (US)

(73) Assignee: BIONIC AIRE INTERNATIONAL CO. LTD., Taipie (TW)

( * ) Notice: Subject to any disclaimer, the term of this patent is extended or adjusted under 35 U.S.C. 154(b) by 420 days.

(21) Appl. No.: 17/494,992

(22) Filed: Oct. 6, 2021

(51) Int. Cl.
   | | |
   |---|---|
   | *H01T 23/00* | (2006.01) |
   | *A61L 9/015* | (2006.01) |
   | *A61L 9/22* | (2006.01) |
   | *F24F 8/30* | (2021.01) |

(52) U.S. Cl.
CPC ............. *H01T 23/00* (2013.01); *A61L 9/015* (2013.01); *A61L 9/22* (2013.01); *F24F 8/30* (2021.01)

(58) Field of Classification Search
None
See application file for complete search history.

(56) References Cited

U.S. PATENT DOCUMENTS

| | | | |
|---|---|---|---|
| 3,960,644 A * | 6/1976 | McFadden | B05B 13/0636 118/713 |
| 5,578,112 A | 11/1996 | Krause | |
| 5,648,046 A | 7/1997 | Weibel | |
| 7,056,372 B2 | 6/2006 | Cheng | |
| 7,740,686 B2 | 6/2010 | Metteer | |
| 7,878,236 B1 | 2/2011 | Breen | |
| 7,906,080 B1 | 3/2011 | Botvinnik | |
| 9,353,966 B2 | 5/2016 | Finkam | |
| 9,696,049 B2 | 7/2017 | Metteer | |
| 10,111,978 B2 | 10/2018 | Waddell et al. | |
| 2007/0022879 A1 | 2/2007 | Aiba | |

FOREIGN PATENT DOCUMENTS

| | | | | |
|---|---|---|---|---|
| AT | 516431 A2 * | 5/2016 | ............. | A61L 9/015 |
| AT | 516431 A2 * | 1/2017 | ............. | A61L 9/015 |

OTHER PUBLICATIONS

AT516431B1-preview (IP.com machine translation of Paschinger) (Year: 2017).*

* cited by examiner

*Primary Examiner* — Gabriel E Gitman
(74) *Attorney, Agent, or Firm* — Birch, Stewart, Kolasch & Birch, LLP

(57) ABSTRACT

A self-powered ionization device is a bipolar plasma ionization module powered by a wind turbine and supported within a unit of HVAC ductwork by at least three adjustable legs. Power generated by an air current within the ductwork operates the bipolar plasma ionization module.

17 Claims, 5 Drawing Sheets

SELF-POWERED IONIZATION DEVICE

RELATED APPLICATIONS

None.

FIELD OF THE INVENTION

The present invention relates generally to an air purification device and specifically to an air purification device that is mounted in an air duct.

BACKGROUND OF THE INVENTION

Recent events in our history, such as the COVID-19 virus, remind us how susceptible humans are to contaminants in the air we breathe. Whether such contaminants are incidental such as dust, dirt, allergens or the like, or something more dangerous such as bacteria and viruses, many people turn to the use of air purification systems for protection.

While portable air purifiers do exist, they only cover a small area inside of a home or business. Additionally, they also take up valuable space in a room and negatively affect the aesthetics of the space. While there are air purifiers which can be installed in a ventilation system, they are large, bulky, require external power and usually require the assistance of a professional to install. Also, most of these duct mounted systems do not lend themselves well to retrofit applications due to space and power requirements. Accordingly, there exists a need for a means by which duct mounted air purification can be provided in a home or business without the disadvantages of current solutions. The development of the self-powered ionization device fulfills this need.

SUMMARY OF THE INVENTION

To achieve the above and other objectives, the present invention provides for a self-powered ionization device having a fan blade shroud which surrounds and protects a plurality of fan blades connected to a central hub, a generator enclosure and an ionization enclosure disposed behind the fan blades, at least three mounting arms which are adapted to mount the self-powered ionization device inside of a piece of ventilation ductwork and each including a base section which mounts to a flange behind shroud supports, a movable section attached to the base section via use of a hinge, and a sliding section disposed on an end of the movable section that contains a spring to keep a mounting foot under constant pressure along an outward travel path, a generator shaft connected to a generator that generates an electrical output, a base plate supporting the generator enclosure and the ionization enclosure, a battery enclosure mounted on an underside of the base plate, and a terminal block disposed on a side of the ionization enclosure for connecting another self-powered ionization device. The generator shaft extending from the central hub to the generator enclosure transmits mechanical power from the fan blades through the flange and into the generator enclosure.

The fan blade shroud may be supported by at least three shroud supports which may connect to a perimeter of the fan blade shroud at a first end of each of the at least three shroud supports. The fan blade shroud may be supported by the at least three shroud supports which may connect to the flange at a second end opposite the first end of the each of the at least three shroud supports. An approaching airflow may activate the fan blades. The at least three mounting arms may be identical. The base section of each of the at least three mounting arms may be connected to the movable section by a hinge pin of the hinge. The hinge pin may allow the movable section and the sliding section to move along a mounting arm travel path to facilitate insertion inside of the piece of ventilation ductwork. The mounting foot on each of the at least three mounting arms may contact an interior surface of the piece of ventilation ductwork. The mounting foot may include a plurality of magnets for attachment of the self-powered ionization device to a metal surface. The electrical output of the generator may be in electrical communication with a voltage regulator by a wiring. The voltage regulator may be in electrical communication with an ionizer inside of the ionization enclosure, the terminal block, and a battery disposed inside of the battery enclosure. An electrical output from the voltage regulator may be 12V DC. The self-powered ionization device may further have a parallel connection from the terminal block to the battery and to the ionizer.

The parallel connection may be made with a wiring. The battery enclosure may operate the self-powered ionization device at times when the fan blades are not operational. The terminal block may be disposed on a side of the ionization enclosure for connecting another ionization enclosure. An ionization device producing an existing ionized airflow may help filter and clean all air downstream of the piece of ventilation ductwork.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which.

Figure 1:
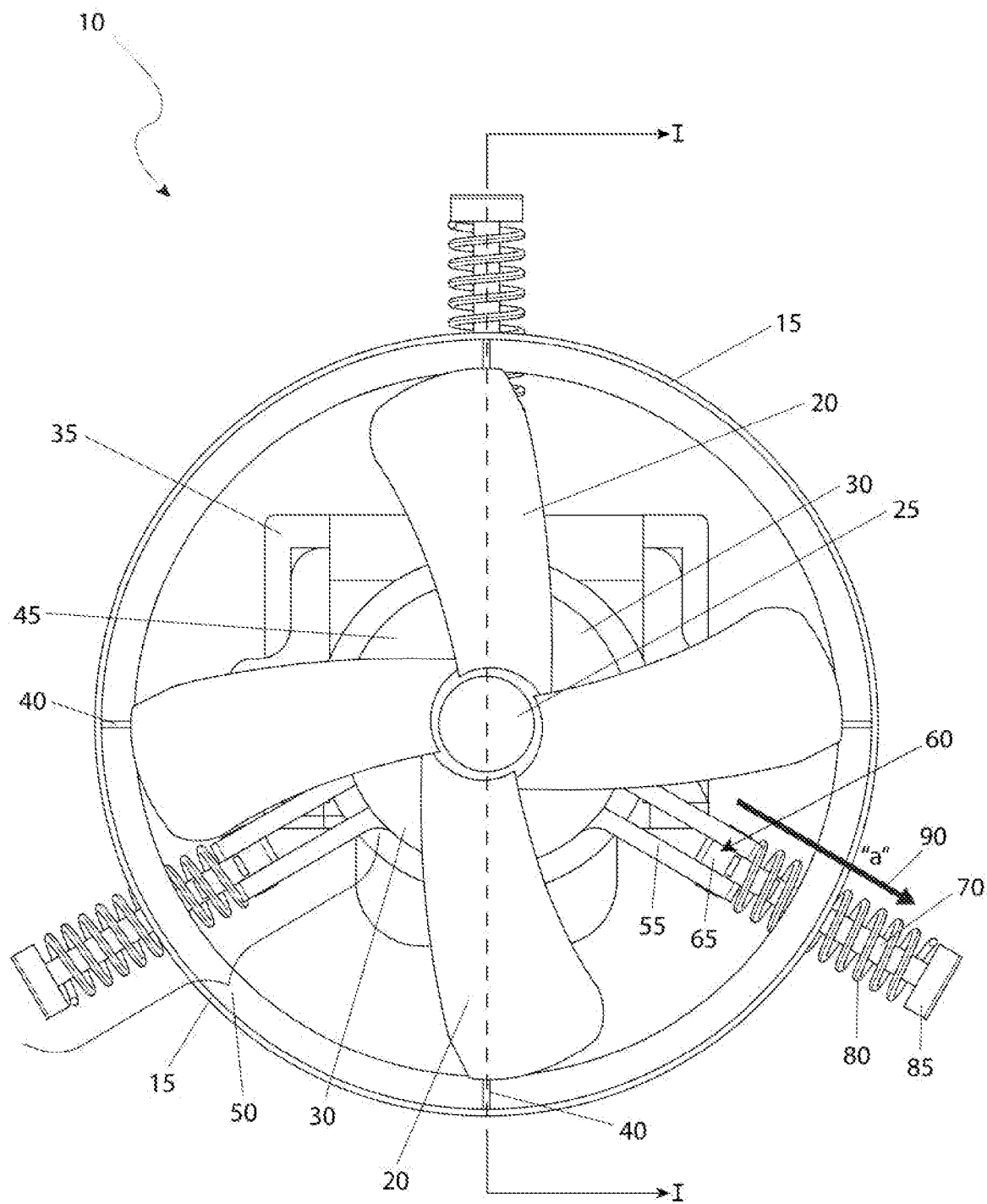
FIG. 1 is a front view of the self-powered ionization device, according to the preferred embodiment of the present invention.

DESCRIPTIVE KEY 10 self-powered ionization device
15 fan blade shroud
20 fan blade
25 hub
30 generator enclosure
35 ionization enclosure
40 shroud support
45 flange
50 mounting arm
55 base section
60 movable section
65 hinge
70 sliding section 80 spring
85 mounting foot
90 outward travel path "a"
95 generator shaft
100 base plate
105 battery enclosure
110 terminal block
115 hinge pin
120 mounting arm travel path "b"
125 generator
130 voltage regulator
135 wiring
140 ionizer
145 battery
150 ductwork
155 duct interior surface
160 approaching airflow
165 exiting ionized airflow

DESCRIPTION OF THE PREFERRED
EMBODIMENTS

The best mode for carrying out the invention is presented in terms of its preferred embodiment, herein depicted within FIGS. 1 through 5. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

DETAILED DESCRIPTION OF THE FIGURES

Referring now to FIG. 1, a front view of the self-powered ionization device 10, according to the preferred embodiment of the present invention is disclosed. The self-powered ionization device (herein also described as the "device") 10 is powered by an approaching airflow 160 moving through the ductwork 150. The device 10 provides for a fan blade shroud 15 which surrounds and protects multiple fan blades 20 connected to a central hub 25. Located behind the fan blades 20 is a generator enclosure 30 and an ionization enclosure 35 which will be described in greater detail herein below. The fan blade shroud 15 is supported by at least three (3) shroud supports 40 which connect to the perimeter of the fan blade shroud 15 at a first end and to a flange 45 at a second end opposite the first end. A set of at least three (3) mounting arms 50 are used to mount the device 10 inside of ventilation ductwork 150 as will be shown herein below. Each mounting arm 50 is comprised of a base section 55, a movable section 60, and a sliding section 70. The base section 55 mounts to the flange 45 behind the shroud supports 40, and the movable section 60 then is attached to the base section 55 via use of a hinge 65, which will be described in greater detail herein below. The sliding section 70 at the end of the movable section 60 contains a spring 80 to keep a mounting foot 85 under constant pressure along an outward travel path "a" 90. The mounting foot 85 may be provided with magnets if needed. All three (3) of the mounting arms 50 are designed in an identical manner.

Figure 2:
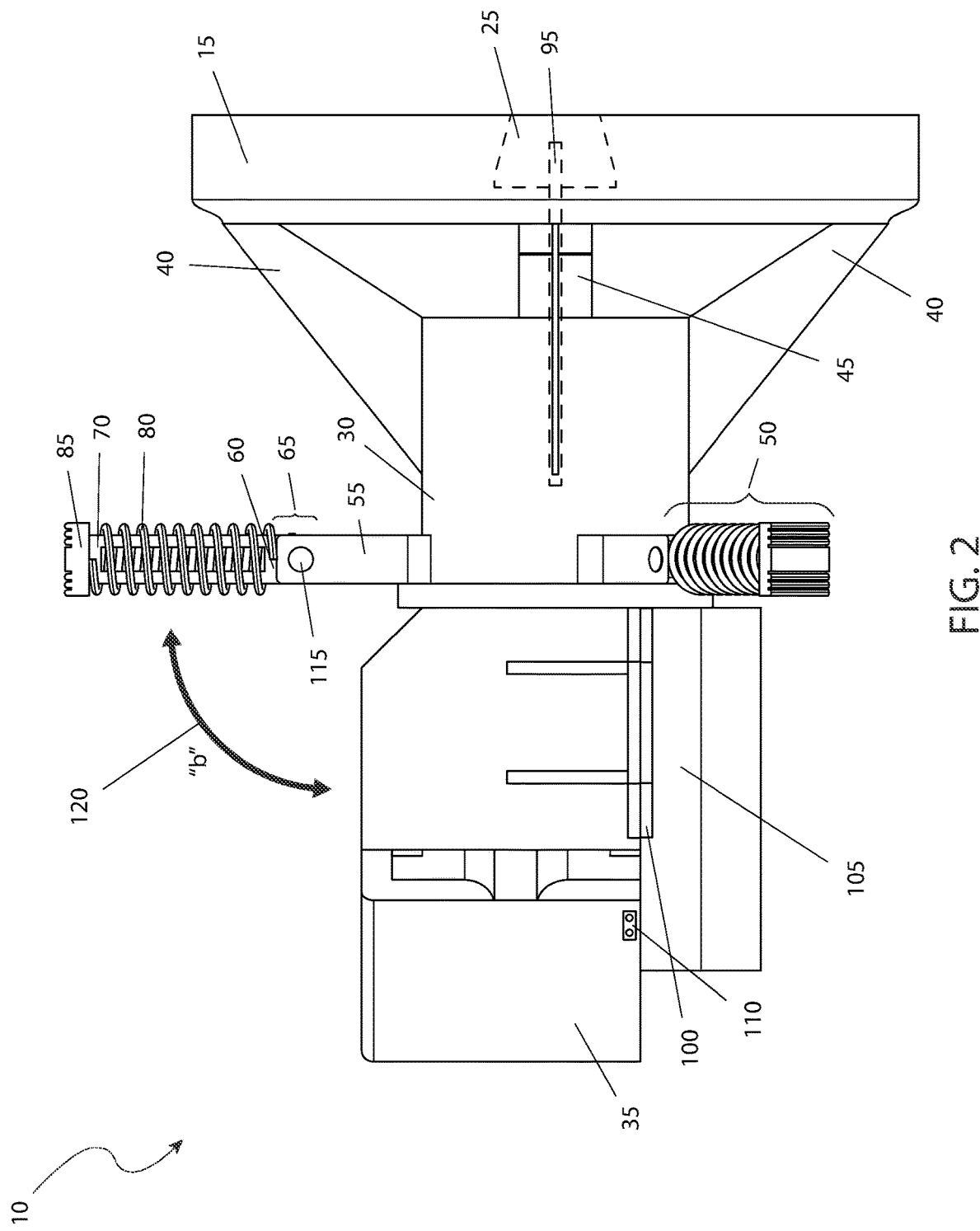
FIG. 2 is a side view of the self-powered ionization device, according to the preferred embodiment of the present invention.

Referring next to FIG. 2, a side view of the device 10, according to the preferred embodiment of the present invention is depicted. This view more clearly depicts the fan blade shroud 15 and the attachment method of the shroud supports 40 from the fan blade shroud 15 to the flange 45. A generator shaft 95 extends from the hub 25 to the generator enclosure 30 and transmits mechanical power from the moving fan blades 20 (as shown in FIG. 1) through the flange 45 and into the generator enclosure 30. A base plate 100 supports the generator enclosure 30 and the ionization enclosure 35. A battery enclosure 105 is mounted on the underside of the base plate 100. The battery enclosure 105 provides for operation of the device 10 at times when the fan blades 20 are not operational. A terminal block 110 is provided on a side of the ionization enclosure 35 for connecting other devices 10 or just to another ionization enclosure 35. The base section 55 of each mounting arm 50 is connected to the movable section 60 by a hinge pin 115 of the hinge 65. The hinge pin 115 allows the movable section 60 and the sliding section 70 to move along a mounting arm travel path "b" 120 to allow for easy insertion inside of ductwork 150 as will be shown below.

Figure 3:
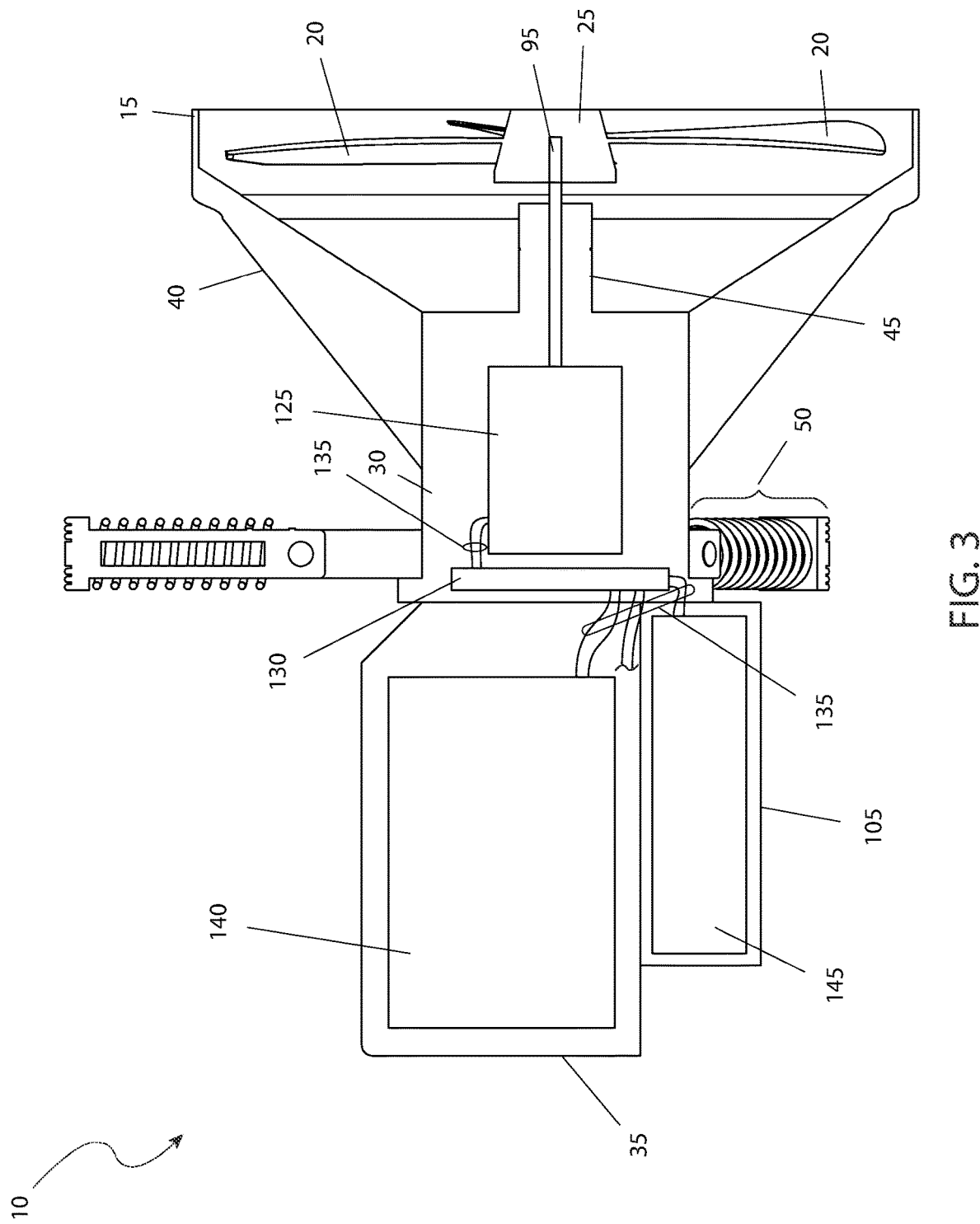
FIG. 3 is a sectional view of the self-powered ionization device, as seen along a Line I-I, as shown in FIG. 1, according to the preferred embodiment of the present invention.

Referring now to FIG. 3, a sectional view of the device 10, as seen along a Line I-I, as shown in FIG. 1, according to the preferred embodiment of the present invention is shown. The generator shaft 95 is shown connecting to a generator 125. As the fan blades 20 (as shown in FIG. 1) turn, the generator shaft 95 turns at a corresponding rate, and operates the generator 125 in a conventional manner. An electrical output of the generator 125 is transferred to a voltage regulator 130 by wiring 135. The output of the voltage regulator 130 is connected to an ionizer 140 inside of the ionization enclosure 35, the terminal block 110 (as shown in FIG. 2), and a battery 145 inside the battery enclosure 105.

Figure 4:
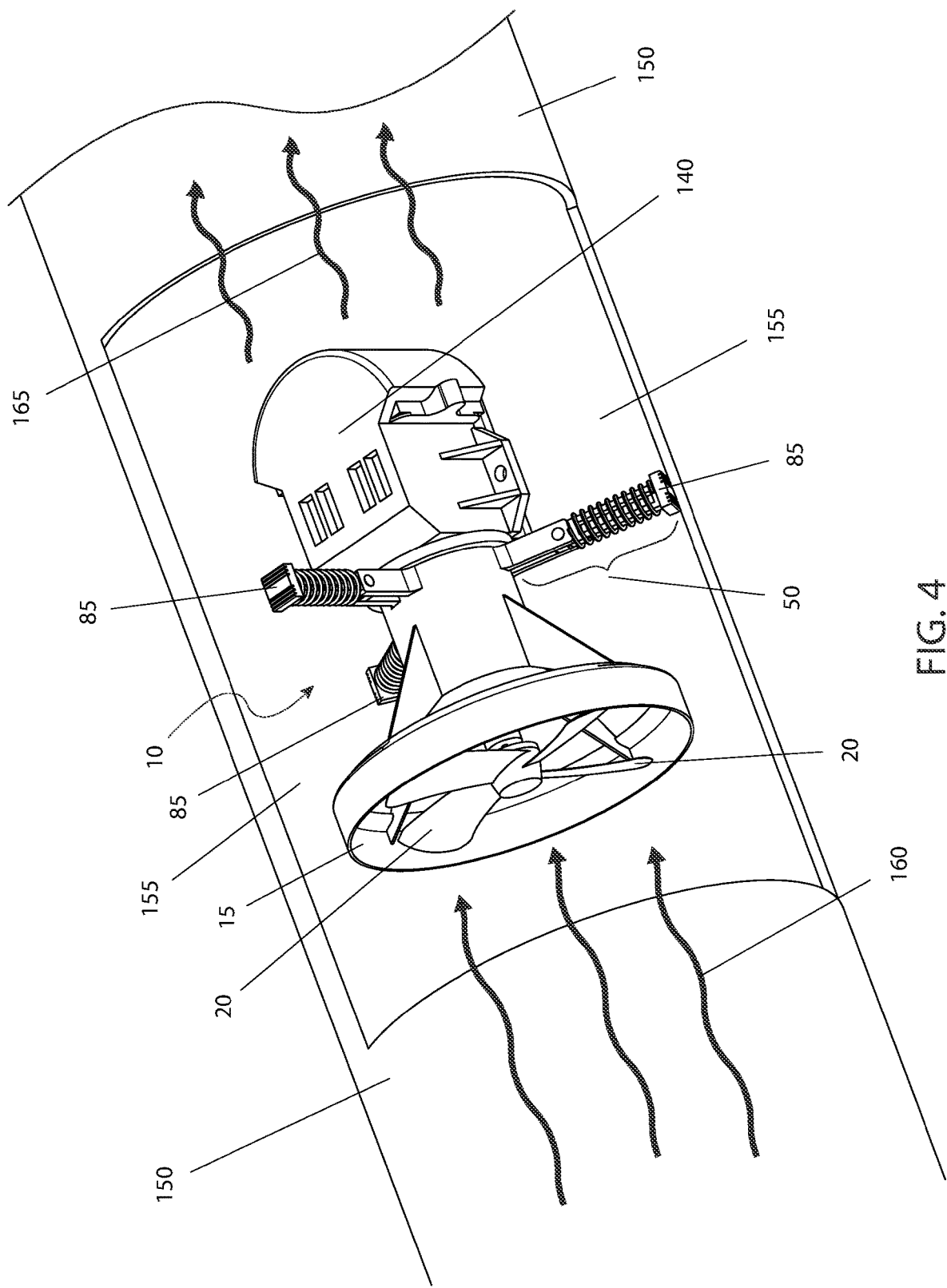
FIG. 4 is a perspective view of the self-powered ionization device, shown in a utilized state, according to the preferred embodiment of the present invention.

Referring next to FIG. 4, a perspective view of the device 10, shown in a utilized state, according to the preferred embodiment of the present invention is disclosed. A cutaway view of a ductwork 150 section allows viewing of the device 10 inside of the ductwork 150. The mounting foot 85 on each of the three (3) mounting arms 50 contacts the duct interior surface 155. Approaching airflow 160 activates the fan blades 20 as aforementioned described. The ionization effect of the ionizer 140 (as shown in FIG. 3) produces an existing ionized airflow 165 that then helps filter and clean all air downstream of the ductwork 150.

Figure 5:
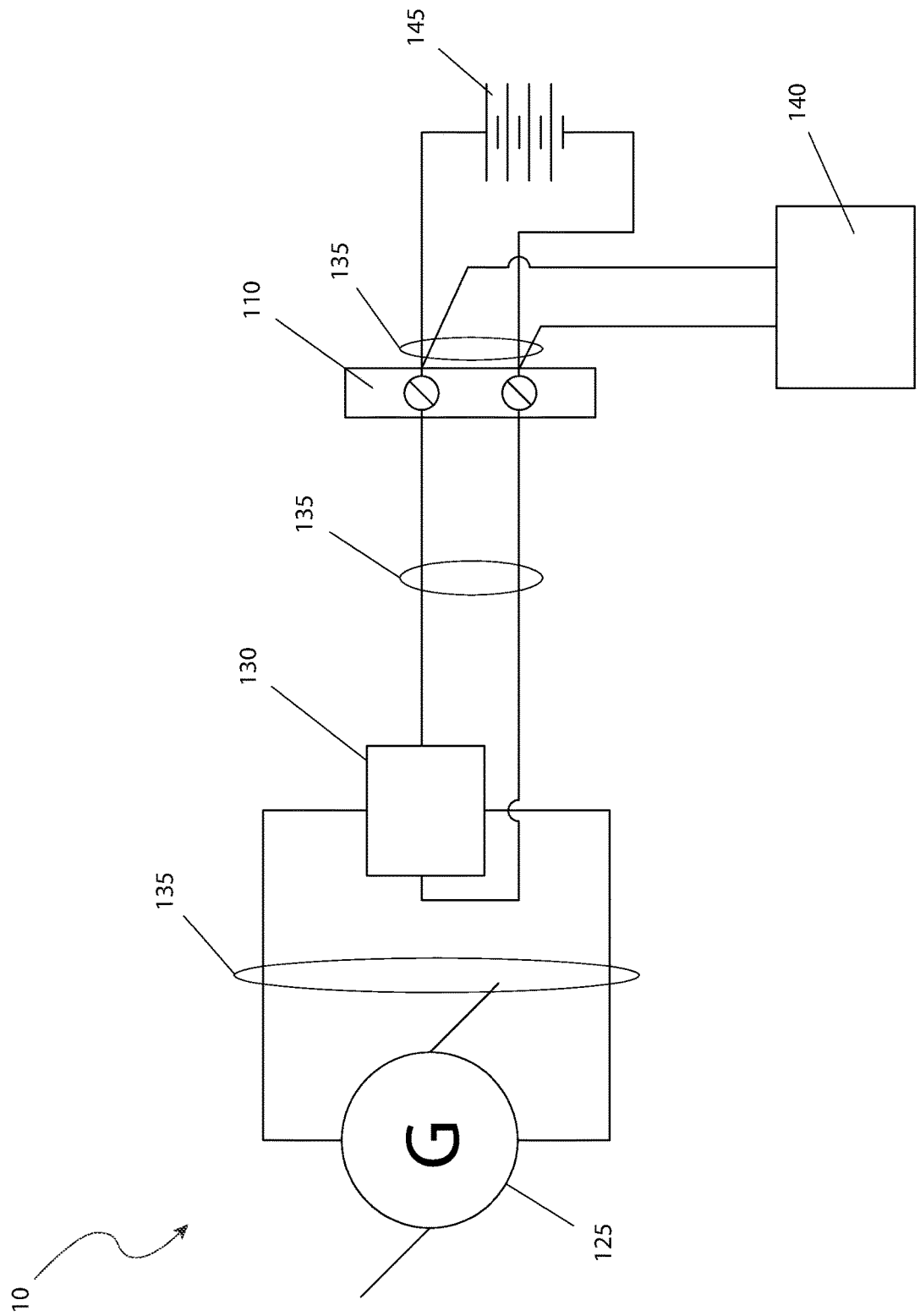
FIG. 5 is an electrical block diagram of the self-powered ionization device, according to the preferred embodiment of the present invention.

Referring finally to FIG. 5, an electrical block diagram of the self-device 10, according to the preferred embodiment of the present invention is depicted. Electrical power produced by the generator 125 is routed to the voltage regulator 130 via the wiring 135. The output of the voltage regulator 130 is routed to the terminal block 110. The device 10 has a parallel connection, using wiring 135 from the terminal block 110 to the battery 145 and to the ionizer 140. It is envisioned that the output of the voltage regulator 130 will be twelve volts direct current (12 VDC), although those familiar in the art will realize that other voltages can be utilized with equal effectiveness. As such, the use of any specific voltage is not intended to be a limiting factor of the present invention. No control of the circuit is provided, as user access to the device 10 once installed in the ductwork 150 (as shown in FIG. 4) is not provided.

OPERATION OF THE PREFERRED EMBODIMENT

The preferred embodiment of the present invention can be utilized by the common user in a simple and effortless manner with little or no training. It is envisioned that the device 10 would be constructed in general accordance with FIG. 1 through FIG. 5. The user would procure the device 10 from conventional procurement channels such as hardware stores, home improvement stores, HVAC supply houses, mail order and internet supply houses and the like. Special attention would be paid to the overall size of the device 10 such that it will fit the desired ductwork 150.

After procurement and prior to utilization, the device 10 would be prepared in the following manner: the user would dissemble a section of ductwork 150 near the desired utilization point, the device 10 would be installed following the configuration as shown in FIG. 4; the mounting arms 50 would be folded backwards along the mounting arm travel path "b" 120 to allow for easy insertion; once at the desired location, the movable section 60 and the sliding section 70 of each mounting arm 50 would be folded perpendicular to the axis of the outward travel path "a" 90 with the sliding section 70 compressed against the spring 80 as needed; with all mounting arms 50 similarly configured, the fan blade shroud 15 and the fan blades 20 would be automatically centered within the ductwork 150. The ductwork 150 would be reassembled at this point. At this point in time, the device 10 is ready for utilization.

During utilization of the device 10, the following procedure would be initiated: once approaching airflow 160 is initiated by the HVAC control system such as for heating, cooling, and/or ventilation, the fan blades 20 will begin to turn in the approaching airflow 160; the generator 125 will then produce power which is the regulated and controlled by the voltage regulator 130. Resultant power is then passed to the ionizer 140 for operation as well as the battery 145 for backup power purposes. The ionizer 140 produces the exiting ionized airflow 165 which allows for immobilization of harmful pathogens such as mold spores, viruses, and bacteria. Said action results in cleaner air and healthier living conditions for those users occupying the space served by the ductwork 150. Said operation continues in an automatic and continuous manner.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A self-powered ionization device, comprising:

a fan blade shroud surrounding and protecting a plurality of fan blades connected to a central hub;

a generator enclosure and an ionization enclosure disposed behind the fan blades;

at least three mounting arms adapted to mount the self-powered ionization device inside of a piece of ventilation ductwork, each of the at least three mounting arms including a base section which mounts to a flange behind shroud supports; a movable section attached to the base section via use of a hinge; and a sliding section disposed on an end of the movable section that contains a spring to keep a mounting foot under constant pressure along an outward travel path;

a generator shaft connected to a generator that generates an electrical output, the generator shaft extending from the central hub to the generator enclosure and transmitting mechanical power from the fan blades through the flange and into the generator enclosure;

a base plate supporting the generator enclosure and the ionization enclosure;

a battery enclosure mounted on an underside of the base plate; and a terminal block disposed on a side of the ionization enclosure for connecting another self-powered ionization device.

2. The self-powered ionization device, according to claim 1, wherein the fan blade shroud is supported by at least three shroud supports which connect to a perimeter of the fan blade shroud at a first end of each of the at least three shroud support.

3. The self-powered ionization device, according to claim 2, wherein the fan blade shroud is supported by the at least three shroud supports which connect to the flange at a second end opposite the first end of each of the at least three shroud supports.

4. The self-powered ionization device, according to claim 1, wherein an approaching airflow activates the fan blades.

5. The self-powered ionization device, according to claim 1, wherein the at least three mounting arms are identical.

6. The self-powered ionization device, according to claim 1, wherein the base section of each of the at least three mounting arms is connected to the movable section by a hinge pin of the hinge.

7. The self-powered ionization device, according to claim 6, wherein the hinge pin allows the movable section and the sliding section to move along a mounting arm travel path to facilitate insertion inside of the piece of ventilation ductwork.

8. The self-powered ionization device, according to claim 1, wherein the mounting foot on each of the at least three mounting arms contacts an interior surface of the piece of ventilation ductwork.

9. The self-powered ionization device, according to claim 1, wherein the mounting foot includes a plurality of magnets for attachment of the self-powered ionization device to a metal surface.

10. The self-powered ionization device, according to claim 1, wherein the electrical output of the generator is in electrical communication with a voltage regulator by a wiring.

11. The self-powered ionization device, according to claim 10, wherein the voltage regulator is in electrical communication with an ionizer inside of the ionization enclosure, the terminal block, and a battery disposed inside of the battery enclosure.

12. The self-powered ionization device, according to claim 11, wherein an electrical output from the voltage regulator is 12 VDC.

13. The self-powered ionization device, according to claim 11, further comprising a parallel connection from the terminal block to the battery and to the ionizer.

14. The self-powered ionization device, according to claim 13, wherein the parallel connection is made with a wiring.

15. The self-powered ionization device, according to claim 1, wherein the battery enclosure operates the self-powered ionization device at times when the fan blades are not operational.

16. The self-powered ionization device, according to claim 1, wherein the terminal block is connectible to another ionization enclosure.

17. The self-powered ionization device, according to claim 1, further comprising an ionizer in the ionization enclosure configured to clean airflow downstream of the piece of ventilation ductwork.

* * * * *